(12) United States Patent
Thompson et al.

(10) Patent No.: US 7,581,451 B2
(45) Date of Patent: Sep. 1, 2009

(54) METHOD AND APPARATUS FOR FLEXURE TESTING TO DISCOVER INCONSISTENCIES IN COMPOSITE STRUCTURES

(75) Inventors: Jeffrey G. Thompson, Kent, WA (US); Andrew J. McCulloch, Renton, WA (US); Carl B. Gifford, Buckley, WA (US)

(73) Assignee: The Boeing Company, Chicago, IL (US)

( * ) Notice: Subject to any disclaimer, the term of this patent is extended or adjusted under 35 U.S.C. 154(b) by 256 days.

(21) Appl. No.: 11/643,122

(22) Filed: Dec. 21, 2006

(65) Prior Publication Data

US 2008/0148863 A1 Jun. 26, 2008

(51) Int. Cl.
*G01N 3/00* (2006.01)
(52) U.S. Cl. .................................. 73/788; 73/12.05
(58) Field of Classification Search ................ 73/12.05, 73/12.07, 12.09, 12.11, 788, 849
See application file for complete search history.

(56) References Cited

U.S. PATENT DOCUMENTS

| | | | | |
|---|---|---|---|---|
| 4,304,133 A | * | 12/1981 | Feamster, III | 73/633 |
| 4,470,293 A | * | 9/1984 | Redmon | 73/12.09 |
| 5,471,868 A | * | 12/1995 | Nolan | 73/84 |
| 5,483,338 A | | 1/1996 | Wachter et al. | |
| 6,138,501 A | * | 10/2000 | Rastegar | 73/82 |
| 6,351,988 B1 | * | 3/2002 | Bartlett | 73/84 |
| 7,075,084 B2 | * | 7/2006 | Thompson et al. | 250/341.6 |
| 7,243,526 B2 | * | 7/2007 | Pringle | 73/12.09 |
| 7,299,686 B2 | * | 11/2007 | Briaud et al. | 73/84 |
| 7,370,538 B2 | * | 5/2008 | Suda et al. | 73/818 |
| 2004/0119019 A1 | * | 6/2004 | Thompson et al. | 250/341.6 |
| 2004/0159790 A1 | * | 8/2004 | Thompson et al. | 250/341.6 |
| 2005/0067569 A1 | | 3/2005 | Shelley et al. | |

OTHER PUBLICATIONS

Powell, G. et al., Nondestructive inspection of heat damage to graphite-epoxy laminates using diffuse reflectance Fourier transform infrared spectroscopy (DRIFTS), 29th International SAMPE Technical Conference, Composites for the Real World; Orlando FL, Oct. 28-Nov. 1, 1997, pp. 766-775.

Kollgaard, J. et al., "Validation of bending stiffness values derived from Lamb wave measurements of heat- degraded laminates," 43rd International SAMPE Symposium, Anaheim CA, May 31-Jun. 4, 1998, pp. 458-469.

Fisher, W. et al., "Laser induced fluorescence imaging of thermal damage in polymer matrix composites," Materials Evaluation, vol. 55, No. 6, Jun. 1997, pp. 726-729.

Heslehurst, R., "Heat damage detection in composite panels using an acoustic hammer," SAMPE 2006, Long Beach CA, Apr. 30-May 4, 2006.

* cited by examiner

*Primary Examiner*—Lisa M Caputo
*Assistant Examiner*—Freddie Kirkland, III
(74) *Attorney, Agent, or Firm*—Gates & Cooper LLP

(57) ABSTRACT

A method and apparatus for detecting and inspecting composite structures to discover inconsistencies by the force and displacement caused by extension of a stylus driven against the composite structure a fixed distance. The measurement of the force on the stylus and the deflection is made from the exterior surface of the composite structure, which eliminates the need to remove interior panels for inspection.

26 Claims, 9 Drawing Sheets

METHOD AND APPARATUS FOR FLEXURE TESTING TO DISCOVER INCONSISTENCIES IN COMPOSITE STRUCTURES

BACKGROUND OF THE INVENTION

1. Field of the Invention

This disclosure relates to systems and methods for inspecting composite structures, and in particular to a system and method for inspecting composite structures for inconsistencies.

2. Description of the Related Art

Composite material has a life cycle much like other materials. Inspection is part of the process used to track the condition of composite materials during its life cycle.

Inconsistencies in the resin of a composite structure may be difficult to detect using nondestructive testing without accompanying inconsistencies in the fibers of the composite. Inconsistencies in the resin of a composite structure may be caused by many sources including, but not limited to, exposure to high temperature for short time periods or moderate temperatures for long periods, lightning strikes and electrical arcing.

At present, there are no approved nondestructive test methods to assess inconsistencies in the resin of composites, particularly thermally induced resin inconsistencies.

Another problem may include the detection of inconsistencies in composite stringers, longerons, frames, spars, caps, and other support structures, for example hat section stringers. In such situations, non-destructive inspection may typically require the time-consuming removal of interior structure, such as panels and/or insulation blankets Accordingly, there is a need for a fieldable in-service method that enables aircraft maintenance personnel to assess and determine the disposition of composite structures that have been thermally exposed or otherwise suspected to be have inconsistencies that might affect performance.

SUMMARY OF THE INVENTION

To address the requirements described above, embodiments of the disclosure illustrate a method and apparatus for analyzing a composite structure for hidden structural inconsistencies. The method comprises the steps of deflecting an interior portion of a test area of the composite structure a fixed distance relative to an exterior portion of the test area by securing a surface of the exterior portion from motion in a first direction and driving a rigid member against a surface of the interior portion at a first location in the first direction, then measuring the force applied to deflect the interior portion of the test area the fixed distance relative to the exterior portion of the test area, and/or measuring the deflection at a distance d from the driven stylus. Next, determining if the composite structure has inconsistencies by comparing the measured force and/or deflection to an expected force and or expected deflection.

In a representative embodiment, the apparatus is a portable, single-sided nondestructive inspection apparatus for analyzing a composite structure, comprising a frame having a horizontal member, a plurality of suction cups attached to the frame and configured to releasably attach the frame to a surface of the composite structure, a drive mechanism, coupled to the horizontal member of the frame, for urging a rigid stylus against the surface of the composite structure at a first location to flex the composite structure, and a force sensor for measuring a force applied to the surface of the composite structure at the first location by the driven stylus and a distance gage for measuring the deflection of the surface at a distance d from the driven stylus.

This foregoing provides a single sided method of detecting inconsistencies caused by thermal exposure or structural effects by monitoring the force and displacement caused by extension of a stylus driven against the composite structure a fixed distance. A measurement of the force on the stylus (and hence the composite structure) and the deflection is made from the exterior surface which eliminates the need to remove interior panels for inspection.

If the structure is without inconsistencies, the structure will be relatively stiff, and the measured force will be large and the displacement, small. If the structure has inconsistencies caused thermal exposure or other factors, the structure below the stylus will flex, and the measured force decreases while the displacement increases. The information generated by these two measurements can be compared to the values from a similar structure in adjacent areas to enable a relative comparison of the severity of the inconsistencies.

This provides a method to quantify thermal inconsistencies to composite material, a method to detect "hidden" inconsistencies in the supporting structure that is not in intimate contact with the exterior skin, and may be hidden by insulation and interior panels. It also can help determine the location of subsurface structures by monitoring the force/extension values taken as the device is moved across a surface.

BRIEF DESCRIPTION OF THE DRAWINGS

Referring now to the drawings in which like reference numbers represent corresponding parts throughout.

DETAILED DESCRIPTION OF PREFERRED EMBODIMENTS

In the following description, reference is made to the accompanying drawings which form a part hereof, and which is shown, by way of illustration, several embodiments of the present invention. It is understood that other embodiments may be utilized and structural changes may be made without departing from the scope of the present invention.

Figure 1:
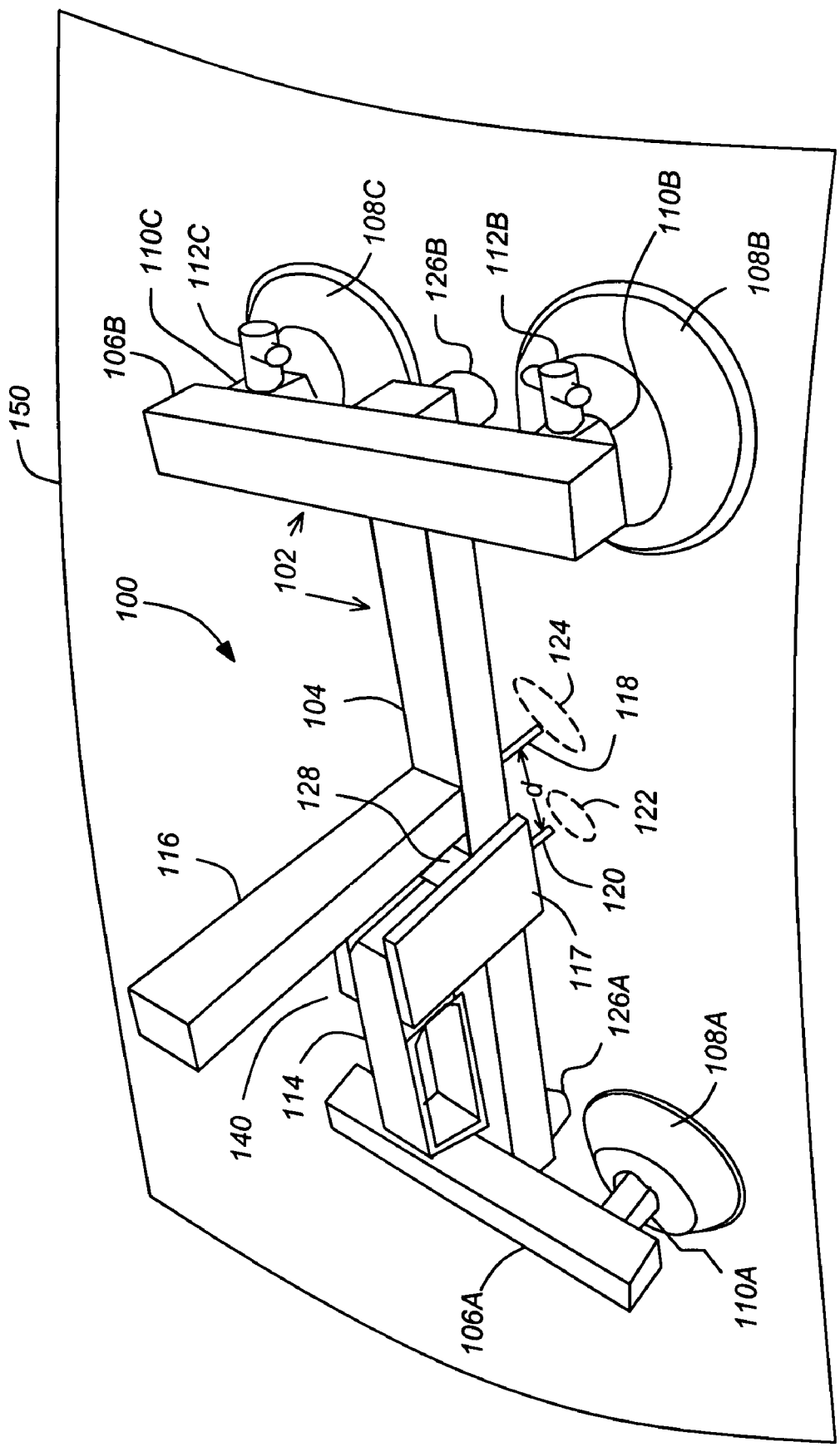
FIG. 1 is an illustration of a perspective view of an exemplary embodiment of an inspection apparatus.

FIG. 1 is an illustration showing a perspective view of an exemplary embodiment of an inspection apparatus 100. In the illustrated embodiment, the inspection apparatus 100 comprises a frame 102 having a horizontal member 104, and a plurality of suction cups 108A-108D hereinafter alternatively referred to as suction cup(s) 108) attached to the frame by members 106, and configured to releasably attach the frame 102 to the surface of a composite structure 150.

The inspection apparatus 100 also comprises a drive mechanism 140 coupled to the horizontal member 104, for urging a rigid stylus 120 against the surface of the composite structure 150 at a first location 122 to flex the composite structure 150 and a force sensor 128 for measuring a force applied to the surface of the composite structure at the first location 122 by the stylus 120. In one embodiment, the drive mechanism 140 employs a structure that causes the rigid stylus 120 to be gently driven or urged against the surface of the composite structure 150 a fixed distance. The drive mechanism 140 can comprise a handle 114 and a cam 202 (illustrated in FIG. 2A), or an equivalent structure such as an elbow joint coupled to a plurality of arms (not shown).

In the illustrated embodiment, the inspection apparatus 100 also comprises a second stylus 118 that is offset from the first stylus 120 by a distance d. The second stylus is in communication with a measurement device 116. The second stylus 118 may be spring loaded so that when the inspection apparatus 100 is attached to the composite structure 150, the second stylus 118 may be in light contact with the composite surface 150. When the first stylus is driven against the composite structure 150, the second stylus 118 remains in contact with the structure 150 so that any displacement of the structure 150 may result in a longitudinal displacement of the stylus 118. The longitudinal displacement of the stylus 118 is measured by the displacement measuring device 116, and used to determine the displacement of the composite surface at a distance d from where the first stylus 120 is driven against the composite structure.

This displacement measurement may also be taken at a location coincident with the first location 112. This can be accomplished by including a displacement measuring device or sensor in the drive mechanism 140.

The inspection apparatus 100 may be secured to the external surface of the composite structure 150 by use of the plurality of suction cups 108, which are attached to a distal end of cross members 106A and 106B. Each suction cup is secured to the frame by bosses 110A-110D. Each of the bosses 110A-110D includes a hollow section therethrough, from which air within the cavity 210A-210D formed by each of the cups 108 can be evacuated. Pneumatic connectors 112A-112D are attached to each of the bosses 110A-110D and the hollow portion of each pneumatic connector 112A-112D is in sealed pneumatic communication with the hollow section of the bosses 112A-112D. Each pneumatic connector 112A-112D also includes nipples that permit the connection of pneumatic tubing so that vacuum can be applied, ultimately evacuating air from the inside cavity of the suction cups 108, affixing them (and thereby, the inspection apparatus 110) to the surface of the composite structure 150.

The illustrated embodiment of the inspection apparatus 100 also includes a plurality of rigid stops 126A-126B coupled to the horizontal member 104. As the air in the inside cavities 210A-210D of the suction cups 108 is evacuated, the apparatus 100 is drawn towards the surface of the composite structure 150. The rigid stops 126 prevent the inspection apparatus 100 from being drawn any closer to the composite structure 150.

Figure 2A:
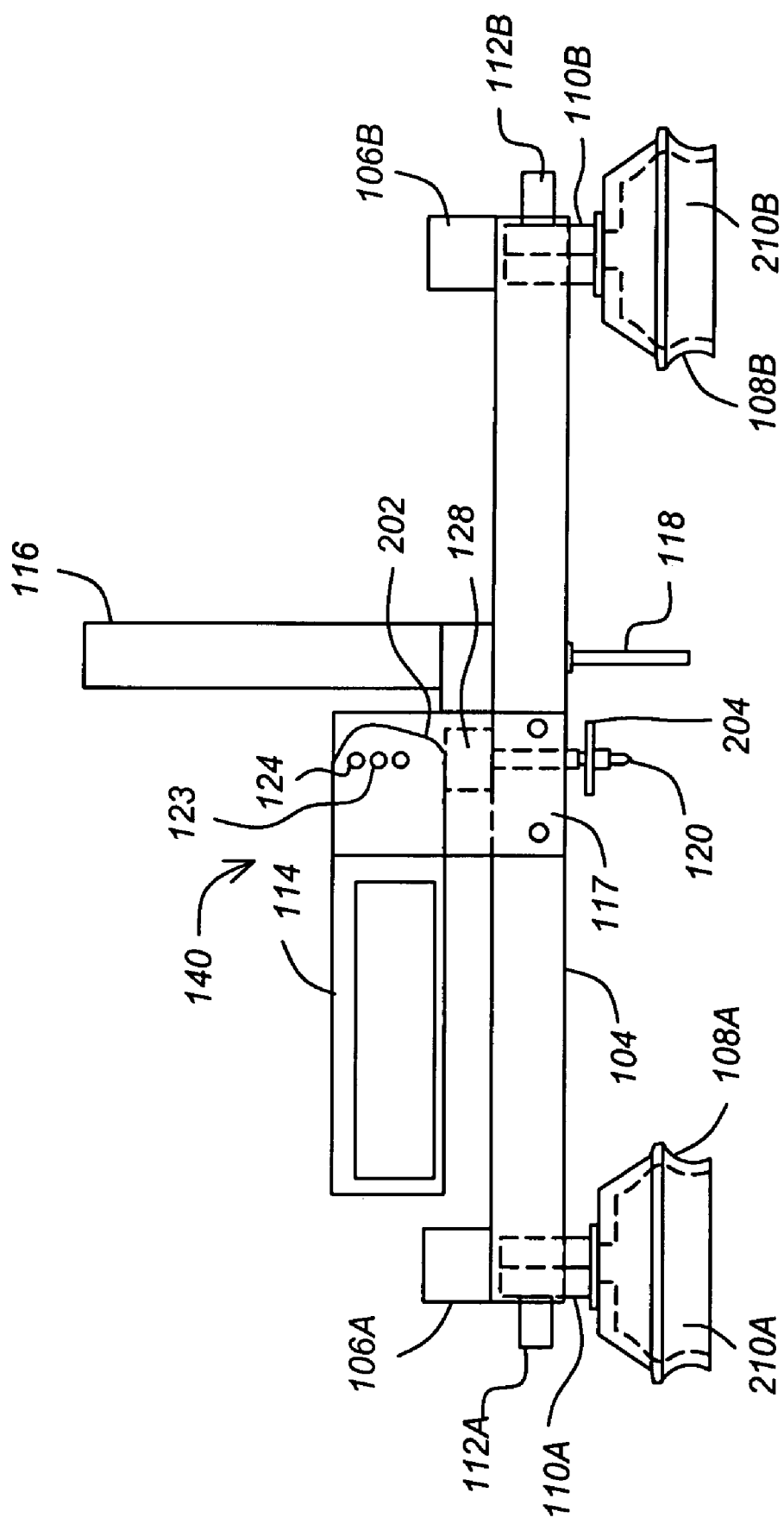
FIGs. 2A-2C are illustrations of side, bottom, and front views of the inspection apparatus shown in FIG. 1.
Figure 2B:
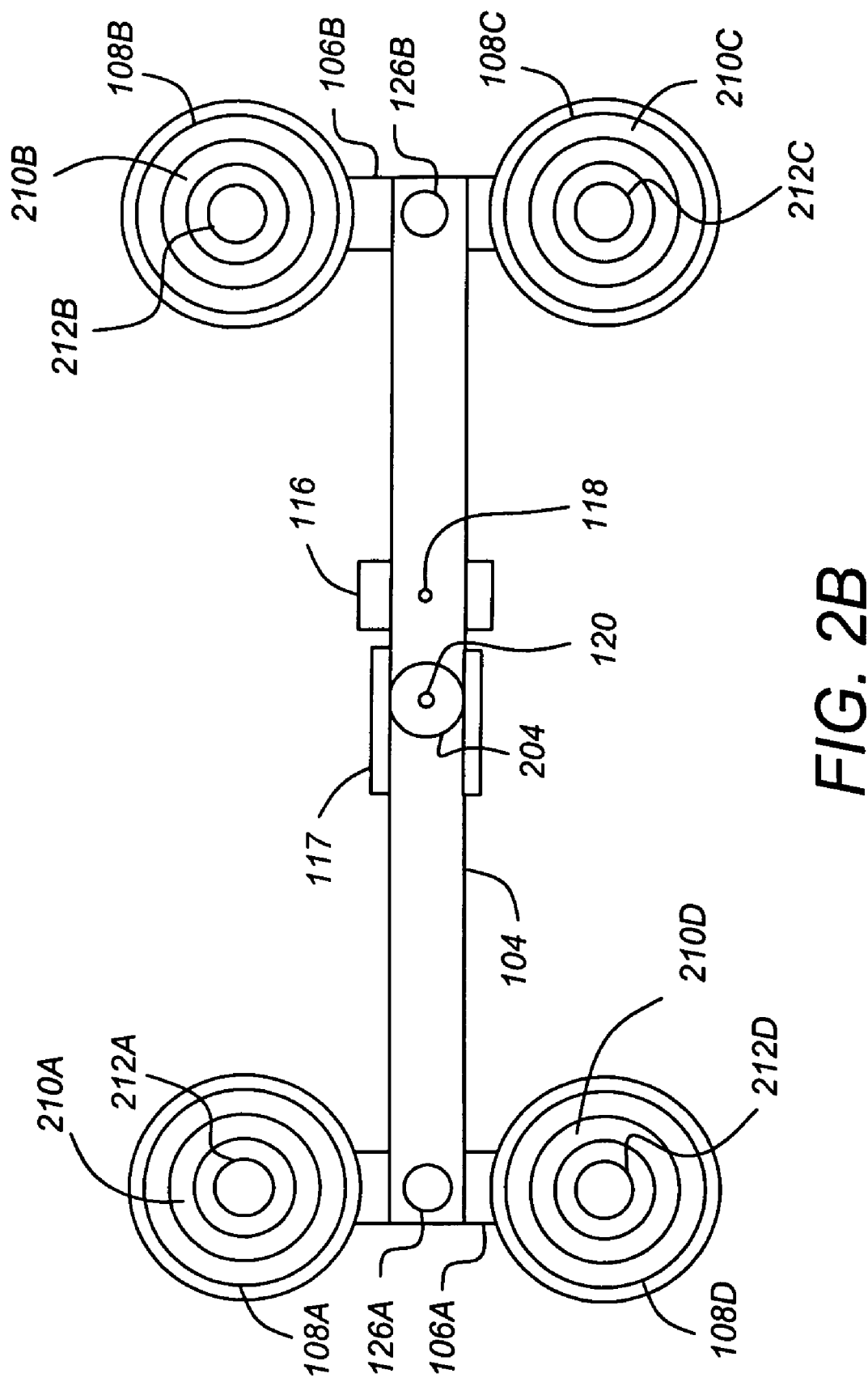
Figure 2C:
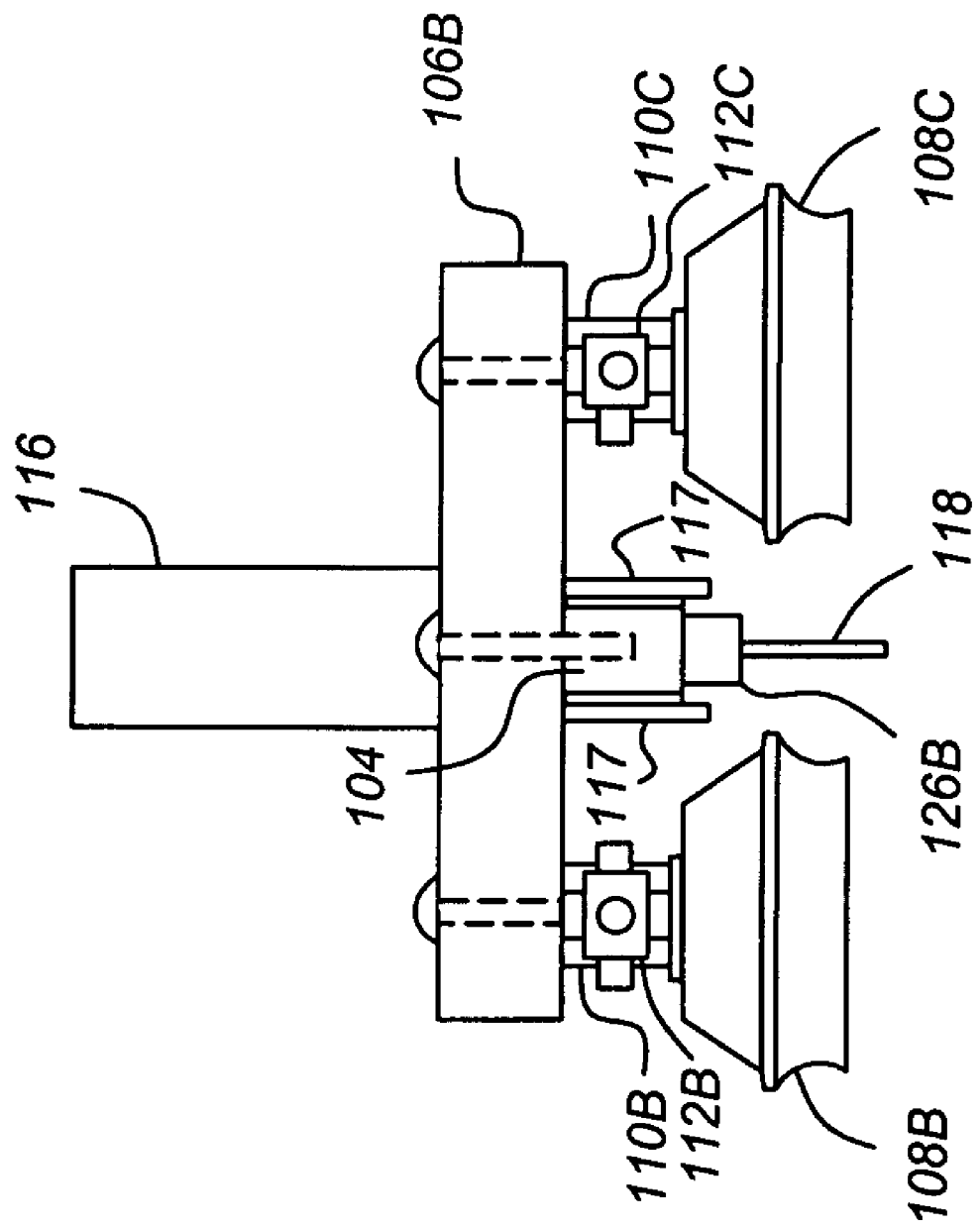

FIGS. 2A-2C are further illustrations of the embodiment shown in FIG. 1. FIG. 2 shows additional details regarding one embodiment of the drive mechanism 140. In this embodiment, the drive mechanism 140 comprises a handle 114 having an integral cam 202. The cam 202 has an eccentric surface and is placed in contact with a force-measuring device 128 such as a load cell. The cam 202 may be secured from all but rotational movement in the plane of the paper by pins 123 that extend through apertures 124. When the handle 114 is lowered, the handle 114 is secured to the location of the aperture 124 by the pin, and thus, rotates around the aperture 124. The eccentric surface of the cam 202 applies a force to the force measuring device 128, which applies the force to the stylus 120, directing the stylus in the downward direction and against the surface of the composite structure 150.

In one embodiment, the surface of the cam 202 is also shaped so that it has a constant radius after being rotated a given amount (instead of an increasing radius before that time), so that the stylus is driven against the surface of the composite structure by a fixed amount (a fixed deflection). This may also be implemented by using a cam 202 having an increasing radius, and adding a stop to the handle 114 or to the drive mechanism supporting structure 117 so that the handle 114 can only be rotated a maximum amount.

There are several apertures in the supporting structure 117 and the handle 114, and by moving the pin 123 to a specific set of apertures 124, the amount of fixed deflection can be selected. The current embodiment has a choice of 0.050", 0.100", 0.150" and 0.200", but other deflections are within the scope of this disclosure.

FIG. 2A also illustrates that the stylus 120 may also comprise a thumbwheel 204 that may be used to extend the length of the stylus as it is mounted in the inspection apparatus 100. This allows the user to attach the inspection apparatus to the surface of the composite structure 105, then, adjust the nominal depth of the stylus (e.g. by rotating thumbwheel 204) so that the stylus 120 contacts the composite structure 150 before the handle 114 is rotated and the load is applied.

FIG. 2B is an illustration of a bottom view of one embodiment of the inspection apparatus 100. FIG. 2B shows the rigid stops 126, and the apertures 212A-212D that permit pneumatic communication between the cavities 210A-210D and the hollow portion of the bosses 110A-110D and hence, the nipples 112A-112D.

FIG. 2C illustrates a side view of the inspection apparatus 100. This view illustrates the spatial relationship between the rigid stops 126 and the suction cups 108, the design of the nipples 112A-112D.

Figure 3:
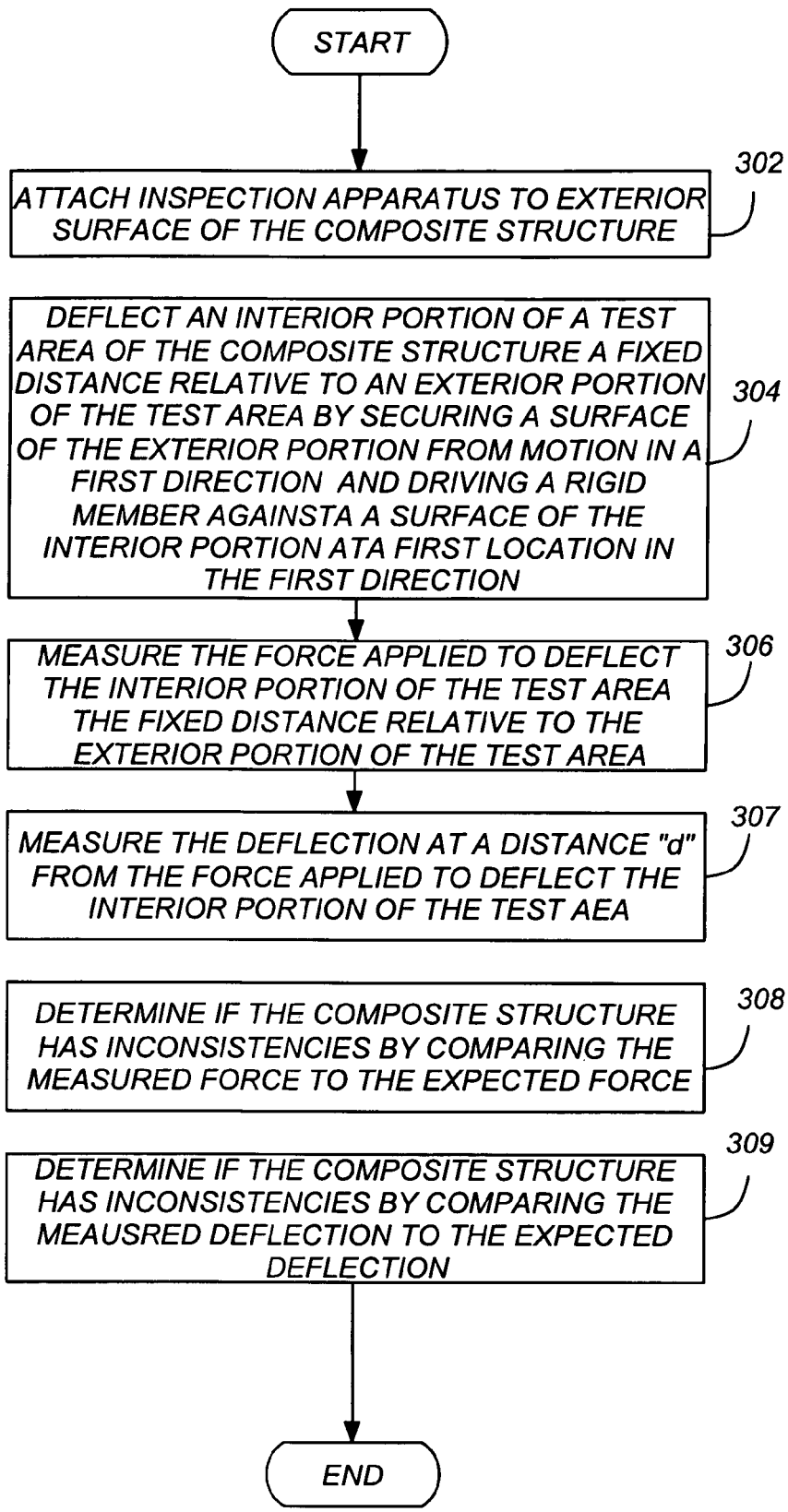
FIG. 3 is a flow chart illustrating exemplary method steps that can be used to practice one embodiment of the present invention.
Figure 4:
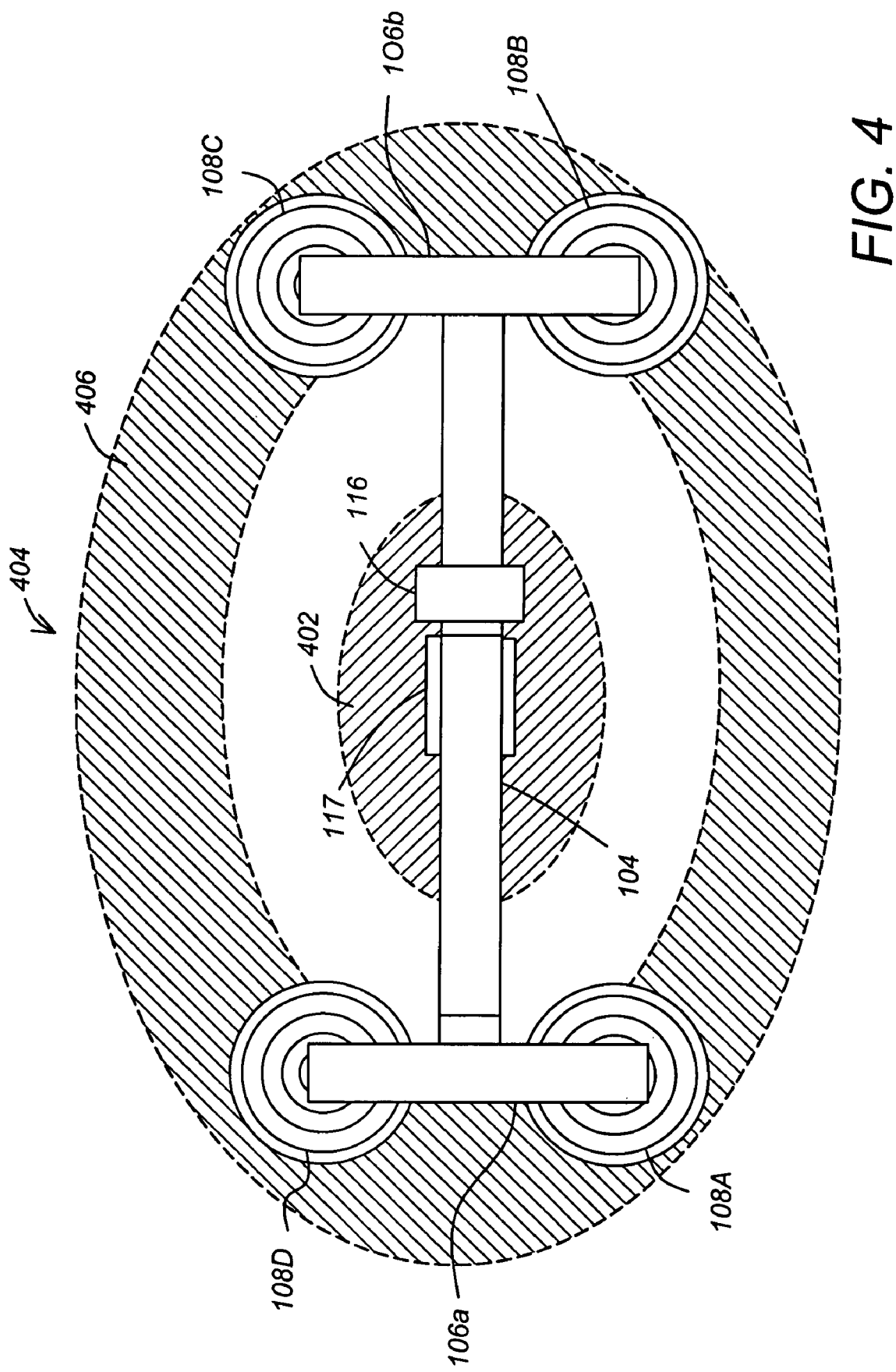
FIG. 4 is an illustration of the application of the inspection apparatus to an external surface of a composite structure.

FIG. 3 is a flow chart illustrating exemplary method steps that can be used to practice an embodiment of the invention. FIG. 3 will be discussed with reference to FIGS. 1, 2A-2C, FIG. 4, which illustrate the application of the inspection apparatus 100 to the composite structure 150, and FIGs. 5A-5E, which illustrate the process.

Figure 5A:
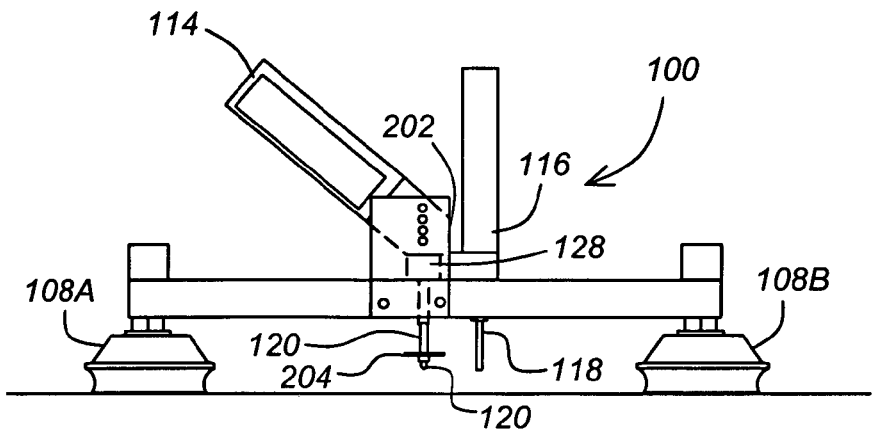
FIGs. 5A-5E are illustrations of the operation of the inspection apparatus.
Figure 5B:
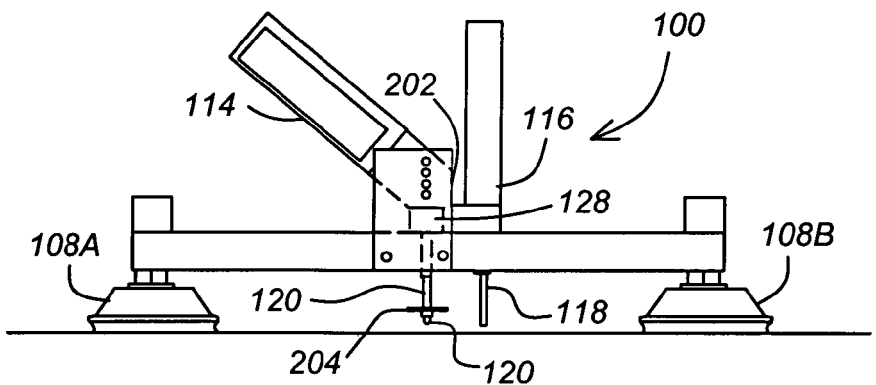
Figure 5C:
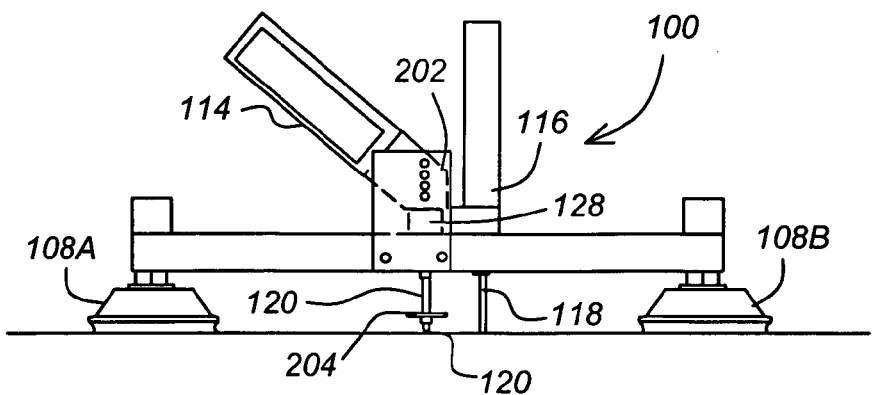

As shown in step 302 of FIG. 3 and in FIGS. 5A and 5B, an inspection apparatus having the suction cups 108 peripherally disposed thereto are attached to the exterior surface of the composite structure 150. This can be accomplished by placing the suction cups 108 against the surface of the composite structure 150 and applying a vacuum to the suction cups 108 to evacuate the suction cup cavities 210A-210D and urge the inspection apparatus towards the surface of the composite structure 150. In one embodiment, the suction cup cavities 210A-210D are evacuated a sufficient amount so that the rigid stops 126 are in contact with the surface of the composite structure 150. As shown in FIG. 5C, the thumbwheel 204 can be used to bring the stylus 120 to contact with the surface of the composite structure 150. The second stylus 118 may also be brought into contact with the composite structure 150.

Figure 5D:
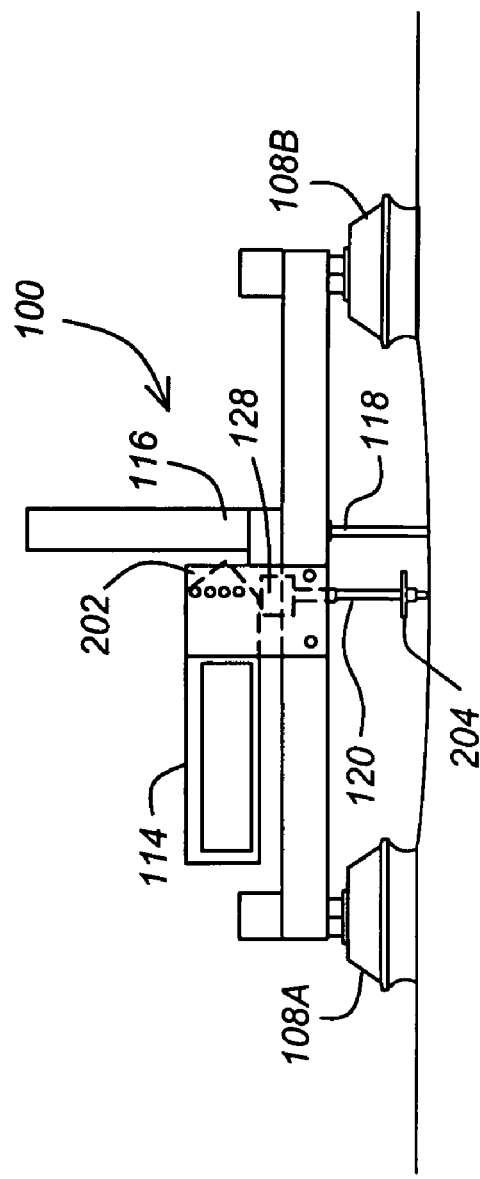

Next, as shown in step 304 of FIG. 3, an interior portion 402 (shown in FIG. 4) of a test area 404 of the composite structure 150 is deflected a fixed distance relative to a portion exterior to the test area 404. This can be accomplished by securing a surface of the exterior portion 406 from motion in a first direction (e.g. in a direction perpendicular to the composite structure 150), and driving a rigid member 120 against a surface of the interior portion 402 of the test area 404 in the same direction, as illustrated in FIG. 5D.

Next, as shown in step 306 of FIG. 3, the force applied to deflect the interior portion 402 (shown in FIG. 4) of the test area 404 the fixed distance relative to the portion 406 external to the test area 404 is measured. This is also illustrated in FIG. 5D. In this embodiment, the force is measured by the sensor 128 disposed between the cam 202 and the stylus 120.

Next, as shown in step 307 of FIG. 3, the deflection of the of the interior portion 402 of the test area 404 is measured at a distance d from the stylus 120 relative to the portion 406 external to the test area 404 is measured. This is also illustrated in FIG. 5D. In this embodiment, the distance is measured by the sensor 116.

Finally, as shown in step 308 of FIG. 3, a determination is made as to whether the composite structure 150 has inconsistencies by comparing the measured force to the expected force and/or the measured deflection to the expected deflection. "Inconsistencies," as the term is used in the appropriate context throughout this disclosure, refers to the difference between one or more measured characteristics of a composite structure under test (and potentially effected by exposure to factor(s) including thermal load(s), structural load(s), lightning, or electrical arcing) with expected values for the same characteristics of an analogous composite structure unaffected by exposure to those factors.

Figure 5E:
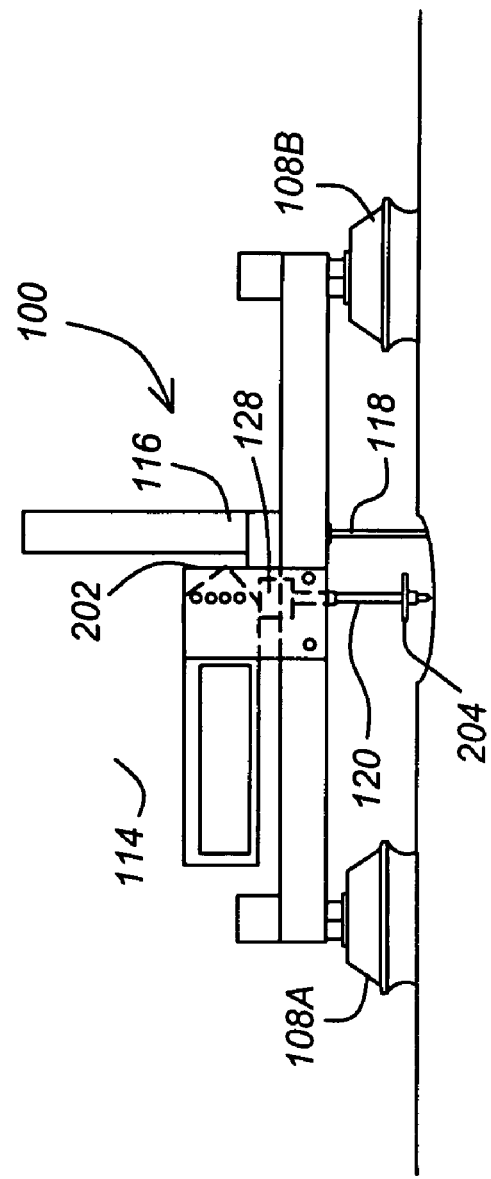

FIG. 5D is a diagram illustrating the typical response of a test area 404 without inconsistencies in the composite structure to the driven stylus, and FIG. 5E is a diagram illustrating the typical response of test area with inconsistencies in the composite structure to a driven stylus. Typically, a composite structure 150 that is without inconsistencies will be stiffer than one that has inconsistencies. Hence, when the stylus 120 is driven the fixed distance against the composite structure to deflect it, the force sensor 112 will register a higher reading for a composite structure 150 (FIG. 5D) without inconsistencies than for a structure with inconsistencies (FIG. 5E). This higher reading is an indication that the underlying structure has inconsistencies.

In the foregoing embodiment, stylus 120 is moved a fixed distance and the force applied to the stylus 120 may be monitored to determine whether the composite structure 150 has inconsistencies. Other embodiments can use a stylus 120 that is driven a variable distance against the composite structure and a deflection measurement device to measure the deflection of the composite structure 150 in response to the driven stylus 120.

For example the drive mechanism 140 may include a vernier scale or other device permitting measurement of the displacement of the stylus 120 driven against the composite structure 150 as well as the force sensor 128 to measure the force applied to the composite structure 150. The relationship between displacement and applied force can be stored and compared to measurements of nearby test areas of the composite structure that are known to be without inconsistencies to assess whether the test area includes inconsistencies.

In addition to or as an alternative to measuring the deflection of the driven stylus 120, a separate deflection measurement device 116 can be used to measure the deflection at a second location laterally offset from the location where the driven stylus 120 contacts the composite structure 150. Since the displacement of the driven stylus 120 is known (it is either fixed or can be measured), the deflection of the composite structure at the second location can be used to provide a measure of the shape of the composite structure 150 when the driven stylus 120 is forced against it's surface, as shown in FIG. 5E. This data can also be compared with expected results to determine whether the composite structure is sufficiently uniform in its pertinent characteristics, or if the inconsistencies in those measure characteristics that require further investigation.

The deflection measurement device 116 can also be used to assure that the rigid stops 126 remain in contact with the surface of the composite structure 150 as the stylus 120 is driven against the composite structure 150, or to provide additional measurement information that can be used to assess possible inconsistencies in the composite structure even if the stops separate from the surface. Typically, if the suction cups 108 become extended and the rigid stops 126 are drawn away from the surface of the composite structure 150, the measured force on the stylus is less than it might have been if suction cup 108 extension had not occurred, but typically, the force is still greater than that which might occur if the composite structure 150 was without inconsistencies.

Figure 6:
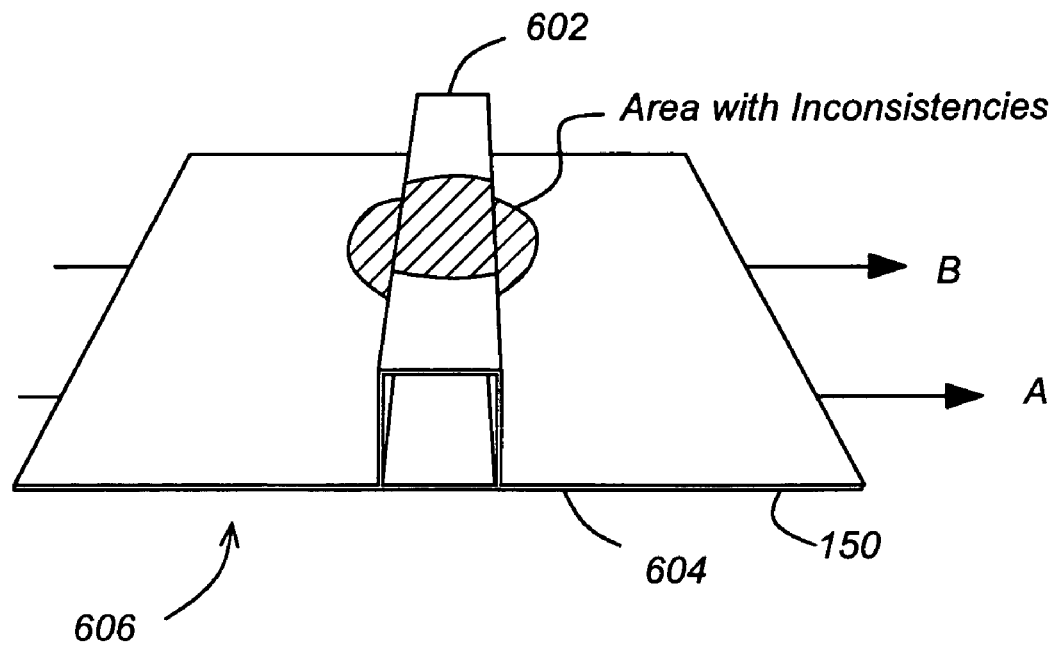
FIG. 6 is an illustration of a further application of the inspection apparatus.
Figure 6:
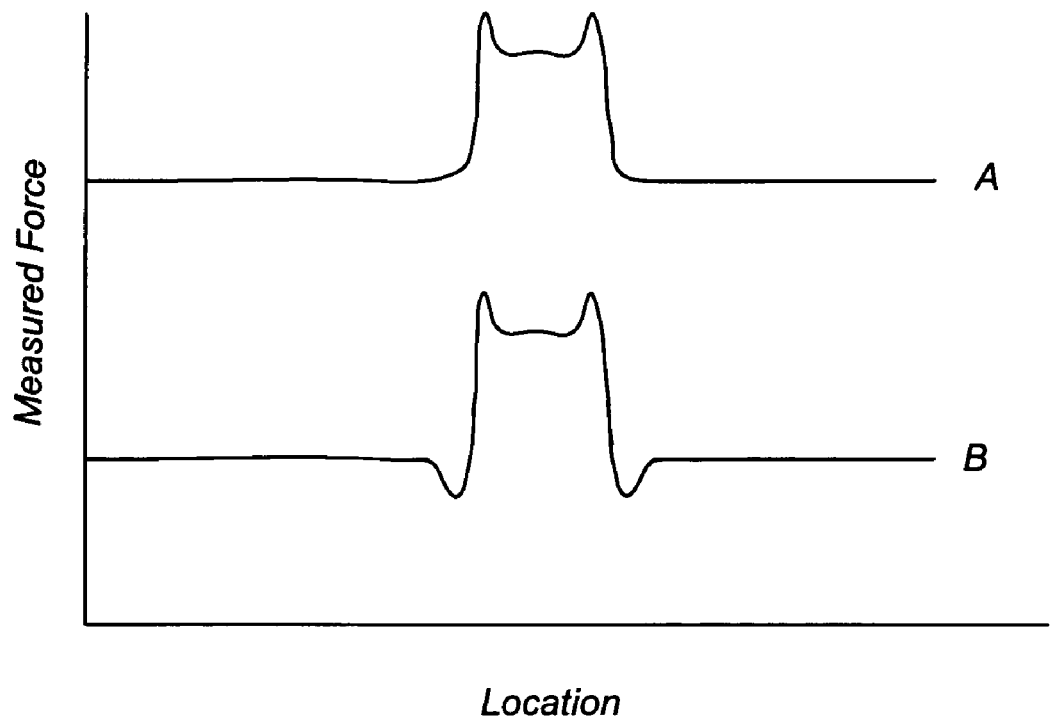

FIG. 6 illustrates the use of the inspection apparatus 100 to externally determine the location of stringers and other structures in multi-layer composite structures. The illustrated composite structure includes one stringer 602 bonded to a sheet of composite material 604, to strengthen the composite material. The location of the stringer is invisible from the external side 606 of the structure 150, however, if the inspection apparatus 100 were passed over different sections of the structure 150 from left to right, the location of the stringer 602 can be determined. For example, if the inspection apparatus 100 were passed in the direction of the arrow labeled "A" while taking measurements as described above, the measured force applied to the stylus might follow a pattern much like that of plot "A", showing increased resistance to deflection in the location where the stringer 602 pattern and the sheet of composite material 604 combine, and less resistance to deflection in those areas where the stringer 602 is not in contact with the sheet of composite material 604. If the inspection apparatus were passed along path "B" over an area of the stringer 603 having inconsistencies, the composite material 604 and stringer 602 combine so that there is less variation in the measured deflection from the driven stylus 120. Using such measurements, the location and configuration of stringers along internal surfaces can be determined. This information can also be used to compare expected forces and deflections with measured values, to determine whether further investigation or replacement is warranted.

CONCLUSION

This concludes the description of the preferred embodiments. The foregoing description of the preferred embodiment has been presented for the purposes of illustration and description. It is not intended to be exhaustive or to limit the invention to the precise form disclosed. Many modifications and variations are possible in light of the above teaching. It is intended that the scope of the rights granted under this disclosure be limited not by this detailed description, but rather by the claims appended hereto. The above specification, examples and data provide a complete description of the manufacture and use of the embodiments. Since many embodiments can be made without departing from the spirit and scope, the claims hereinafter appended are submitted for consideration.

What is claimed is:

1. A method for detecting inconsistencies in a composite structure, comprising the steps of:

deflecting an interior portion of a test area of the composite structure a distance relative to an exterior portion of the test area by securing a surface of the exterior portion from motion in a first direction and driving a member against a surface of the interior portion at a first location in the first direction;

measuring the force applied to deflect the interior portion of the test area the distance relative to the exterior portion of the test area;

measuring the deflection of the test area at a second location laterally offset from the first location; and determining if the composite structure has inconsistencies by comparing the measured force to an expected force, comprising the step of comparing the measured deflection with an expected deflection.

2. The method of claim 1, wherein the surface of the exterior portion of the composite structure releasably coupled to the surface of the exterior portion of the composite structure.

3. The method of claim 2, further comprising the steps of:

releasably coupling an inspection apparatus having at least one suction cup peripherally disposed thereto to the surface of the exterior portion;

applying a vacuum to each said suction cup to urge the inspection apparatus towards the surface of the composite structure.

4. The method of claim 3, wherein:

the inspection apparatus further comprises at least one stop disposed such that when the vacuum is applied, each said stop is in contact with the surface of the composite structure.

5. The method of claim 4, wherein:

the method further comprises the step of measuring the deflection of the test area to determine if the stops remain in contact with the surface of the composite structure; and the step of determining if the composite structure has inconsistencies further comprises comparing the measured deflection of the test area to the expected deflection.

6. The method of claim 1, wherein the composite structure comprises a plurality of fibers and resin.

7. A portable, single-sided nondestructive inspection apparatus for analyzing a composite structure, comprising:

a frame having a horizontal member;

a plurality of suction cups attached to the frame and configured to releasably attach the frame to a surface of the composite structure;

a drive mechanism, coupled to the horizontal member of the frame, for urging a stylus against the surface of the composite structure at a first location;

a force sensor for measuring a force applied to the surface of the composite structure at the first location by the driven stylus; and a second stylus, offset from the first stylus by a distance, the second stylus which records a displacement of the surface of the composite structure at a second location resulting from the urging of the second stylus against the surface of the composite structure.

8. The apparatus of claim 7, wherein the drive mechanism urges the rigid stylus against the surface of the composite structure a fixed distance.

9. The apparatus of claim 8, wherein the drive mechanism comprises a cam.

10. The apparatus of claim 9, wherein the force sensor comprises a load cell mounted between the cam and the stylus.

11. The apparatus of claim 10, further comprising a vacuum generator, pneumatically coupled to the suction cups.

12. The apparatus of claim 11, wherein the vacuum generator is selected from a group comprising:

a pump; and a venturi and a source of gas flow.

13. The apparatus of claim 7, wherein the composite structure comprises a plurality of fibers and resin.

14. An apparatus for detecting inconsistencies in a composite structure, comprising:

means for deflecting an interior portion of a test area of the composite structure a distance relative to an exterior portion of the test area, comprising:

means for securing a surface of the exterior portion from motion in a first direction and means for driving a member against a surface of the interior portion at a first location in the first direction;

means for measuring the force applied to deflect the interior portion of the test area the distance relative to the exterior portion of the test area;

means for measuring the deflection of the test area at a second location laterally offset from the first location; and means for determining if the composite structure has inconsistencies by comparing the measured force to an expected force, comprising means for comparing the measured deflection with an expected deflection.

15. The apparatus of claim 14, wherein the means for securing a surface of the exterior portion from motion in a first direction comprises suction cups releasably coupleable to the surface of the exterior portion of the composite structure.

16. The apparatus of claim 15, further comprising:

means for applying a vacuum to the suction cups to urge the inspection apparatus towards the surface of the composite structure.

17. The apparatus of claim 16, wherein:

the inspection apparatus further comprises at least one stop disposed proximate the suction cups, and the vacuum is applied until each said stop is in contact with the surface of the composite structure.

18. The apparatus of claim 17, wherein:

the apparatus further comprises means for measuring the deflection of the test area to determine if the stops remain in contact with the surface of the composite structure; and the means for determining if the composite structure has inconsistencies further comprises means for comparing the measured deflection of the test area to the expected deflection.

19. The apparatus of claim 14, wherein the composite structure comprises a plurality of fibers and resin.

20. A method for detecting inconsistencies in a composite structure, comprising the steps of:

deflecting an interior portion of a test area of the composite structure a distance relative to an exterior portion of the test area by securing a surface of the exterior portion from motion in a first direction and driving a member against a surface of the interior portion at a first location in the first direction;

measuring the deflection of the test area at a second location laterally offset from the first location; and determining if the composite structure has inconsistencies further comprises the step of comparing the measured deflection with an expected deflection.

21. The method of claim 20, wherein the method further comprises the step of measuring the force applied to deflect the interior portion of the test area the distance relative to the exterior portion of the test area; and determining if the composite structure has inconsistencies by comparing the measured force to an expected force.

22. The method of claim 20, wherein the surface of the exterior portion of the composite structure is secured from motion via suction cups releasably coupleable to the surface of the exterior portion of the composite structure.

23. The method of claim 22, further comprising the steps of:
   attaching an inspection apparatus having the suction cups peripherally disposed thereto to the surface of the exterior portion;
   applying a vacuum to the suction cups to urge the inspection apparatus towards the surface of the composite structure.

24. The method of claim 23, wherein:
   the inspection apparatus further comprises rigid stops disposed proximate the suction cups and the vacuum is applied until the rigid stops are in contact with the surface of the composite structure.

25. The method of claim 24 wherein:
   the method further comprises the step of measuring the deflection of the test area to determine if the rigid stops remain in contact with the surface of the composite structure; and
   the step of determining if the composite structure has inconsistencies further comprises comparing the measured deflection of the test area to the expected deflection.

26. The method of claim 20, wherein the composite structure comprises a plurality of fibers and resin.

* * * * *